United States Patent [19]

Smiley et al.

[11] Patent Number: 4,484,895
[45] Date of Patent: Nov. 27, 1984

[54] INTEGRATED ORAL MAGNETIC OSTEOGENIC APPLIANCES

[75] Inventors: Harry Smiley, White Plains; Abraham Blechman, Tappan, both of N.Y.

[73] Assignee: Medical Magnetics, Inc., Ramsey, N.J.

[21] Appl. No.: 538,491

[22] Filed: Oct. 3, 1983

Related U.S. Application Data

[63] Continuation-in-part of Ser. No. 322,423, Nov. 18, 1981, Pat. No. 4,424,030, which is a continuation of Ser. No. 019,427, Mar. 12, 1979, abandoned.

[51] Int. Cl.³ .............................................. A61C 5/04
[52] U.S. Cl. ...................................... 433/215; 128/1.3; 433/6; 433/18
[58] Field of Search .......................... 433/6, 18, 215; 128/1.3; 317/123

[56] References Cited

U.S. PATENT DOCUMENTS

| | | | |
|---|---|---|---|
| 3,984,915 | 10/1976 | Noble | 433/18 |
| 4,017,973 | 4/1977 | Nelson | 433/18 |
| 4,396,373 | 8/1983 | Dellinger | 433/6 |

Primary Examiner—Robert Peshock
Attorney, Agent, or Firm—Hopgood, Calimafde, Kalil, Blaustein & Judlowe

[57] ABSTRACT

The invention contemplates a unitary intra-oral positioning fixture for use in orthodontic and/or periodontal therapy and bone augmentation. The fixture provides compliant support for two coacting sources of magnetic flux, respectively positioned on the lingual and buccal sides of a region of a tooth or teeth (and adjacent alveolar bone) requiring osteogenesis and soft-tissue repair.

23 Claims, 10 Drawing Figures

INTEGRATED ORAL MAGNETIC OSTEOGENIC APPLIANCES

BACKGROUND OF THE INVENTION

This application is a continuation-in-part of our co-pending application Ser. No. 322,423, filed Nov. 18, 1981 now U.S. Pat. No. 4,424,030 issued 1/03/84, which is a continuation of our original application, Ser. No. 019,427, filed Mar. 12, 1979 (now abandoned).

Said applications disclose various embodiments of magnetic osteogenic and orthodontic appliances, in which relative movement of magnetic devices produces varying currents in localized regions in aid of soft-tissue repair and osteogenesis. Some of the disclosed arrangements utilize magnetic devices for essentially only orthodontic purposes, while others are primarily adapted for soft-tissue repair and osteogenesis. Among the disclosed arrangements is an intra-oral positioning fixture comprising labial, buccal and lingual flanges and defining a channel adapted to span corresponding buccal and lingual areas of alveolar bone requiring osteogenesis and soft-tissue repair wherein separate sources of magnetic flux carried by the buccal and lingual flanges are adapted for coaction with each other via said areas of alveolar bone.

BRIEF STATEMENT OF THE INVENTION

It is an object of the invention to provide improved and further intra-oral positioning fixtures of the character indicated, adapted to therapeutically expose a magnetic field of desired character to a region of the periodontium, i.e., alveolar bone and and adjacent tissue requiring osteogenesis and/or soft-tissue repair.

It is one specific object to provide improved means whereby therapeutically beneficial varying magnetic fields may be produced by such a fixture, without resort to an external source of energy.

It is another specific object to provide improved means whereby such a fixture may provide a therapeutically beneficial non-varying magnetic field, with or without selective variation of the magnetic field.

Still another object is to achieve the above objects with non-invasive structure having removable, self-retaining positioning support within the mouth.

In a preferred form, the invention achieves the foregoing objects by providing a positioning fixture having buccal and lingual flanges which are adjacent corresponding buccal and lingual areas of the periodontium requiring osteogenesis and soft-tissue repair, there being separate sources of magnetic flux carried by the buccal and lingual flanges and magnetically coacting with each other via said areas.

DETAILED DESCRIPTION

The invention will be illustratively described in detail in conjunction with the accompanying drawings, in which.

Figure 1:
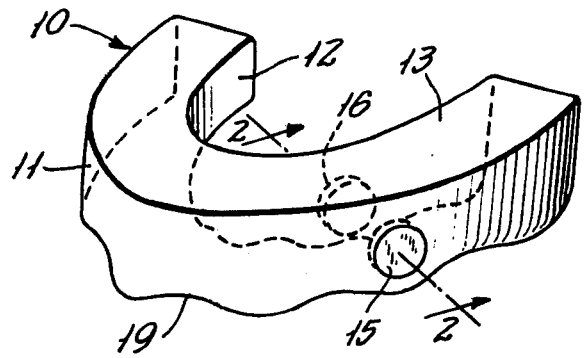
FIG. 1 is a perspective view of a positioning fixture of the invention.
Figure 2:
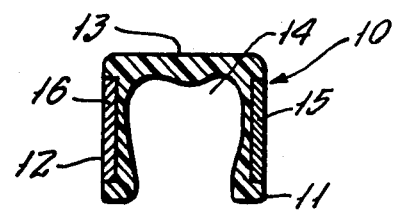
FIG. 2 is a sectional view taken at 2—2 in FIG. 1.

In FIGS. 1 and 2, the invention is shown in application to a positioning fixture 10 of suitably compliant bio-compatible plastic or elastomeric material, generally characterized by buccal and lingual flanges 11-12 which are integrally connected by an occlusal flange 13. The flanges 11-12-13 define a channel 14 which, in the form shown, is downwardly open and conforms to and spans the course of teeth and the periodontium, including the alveolar bone, of the lower jaw or mandible; and it will be understood that similar structure, inverted to provide an upwardly open channel, may similarly conform to the course of teeth and alveolar bone of the upper jaw.

The flanges 11-12-13 of fixture 10 are the product of custom-molding to the individual tooth and jaw features of the particular patient. Thus, the inner surfaces of the buccal and lingual flanges converge in the direction of the channel opening (as seen in FIG. 2), in conformance with involved tooth profiles, to establish a naturally hugging engagement with and retention to involved teeth, while permitting selective removability, by reason of the compliant nature of the material of the flanges.

In accordance with a feature of the invention, first and second sources 15-16 of magnetic flux are carried by or embedded in the respective buccal and lingual flanges 11-12. As shown, each of the sources 15-16 is a permanent magnet, in the shape of a thin circular disc, of suitably half-inch or one-centimeter diameter and of thickness which is a small fraction of the diameter, as in the range of 10 to 25 percent of the diameter. Preferably, each of the magnets 15-16 is polarized on its axis, thus establishing the circular end faces of each magnet as opposite poles, and the placement of magnets 15-16 is in mutually facing relation across that part of the channel 14 where periodontal therapy and/or alveolar-ridge maintenance is needed.

If the opposed adjacent faces of magnets 15-16 are of opposite polarity, a strong uniform flux field is established across the region of desired tissue therapy or maintenance, with therapeutically beneficial effectiveness over approximately six or more months, when worn with daily consistency, if not continuously. The exact mechanism of cell reaction to the strong flux field is not as yet fully understood, but it is presently believed that the degree of compliant yieldability of the fixture (10) material enables magnets 15-16 to be subject to periodic cycles of small displacement with respect to each other and with respect to the region of tissue therapy, as by reason of bite action, thus establishing concomitant variations in flux field through the tissue region, with accompanying induction of therapeutically beneficial, albeit low-level, voltages and currents in affected tissues and/or cells.

If, on the other hand, the opposed adjacent faces of magnets 15-16 are of the same polarity, then repulsion action between the magnets forces mushroom-like flux concentrations at and surrounding both the involved lingual and buccal regions of the teeth and alveolar bone. The same compliant yieldability exists in the material of fixture 10, and therefore the same belief is held that small displacements of the respective magnets enables local induction of beneficial voltages and currents in affected tissues and/or cells.

Figure 2A:
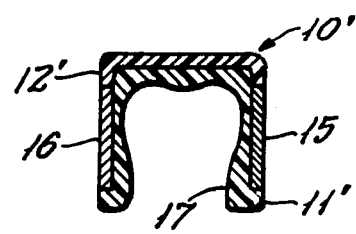
FIG. 2A is a view similar to FIG. 2, to show a modification.

The modification of FIG. 2A illustrates that the supportive fixture of the invention may in fact comprise two parts, namely, an outer channel-shaped shell 10' which is preformed with thin walls (flanges 11'-12') which mount the sources 15-16 of magnetic flux, and a lining 17 which is custom molded to the involved buccal and lingual profiles of the patient. The preformed shell 10' may be of acrylic material, being one of a series of standardized shapes and sizes to accommodate a range of patients' individual requirements, with small clearance for molded development of the lining 17. The series of shapes may include premounted pairs of magnets 15-16, at particular standardized locations along the course of jaw; alternatively, the dentist may be supplied with a suitable punch and/or adhesive means for mounting the magnets 15-16 at buccal and lingual regions he has professionally determined to be most applicable to his patient's need. In either event, the lining 17 will effectively seal inner adjacent faces of magnets 15-16 against exposure to body or other fluids, and preference is indicated for a protective coating of biocompatible material, such as an acrylic, expoxy, urethane or other suitable adhesive at least over the outer faces of magnets 15-16.

Figure 3:
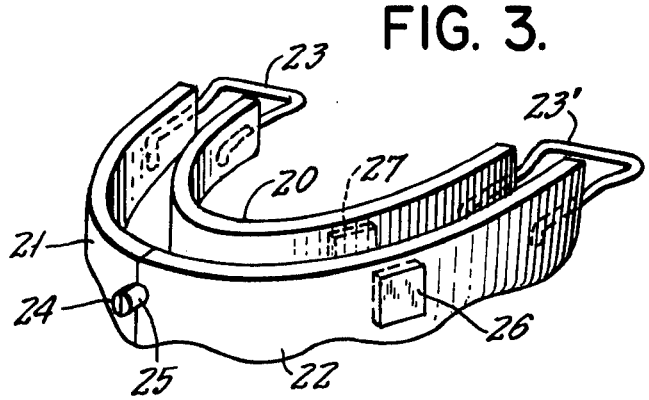
FIG. 3 is a view similar to FIG. 1, to show another embodiment.

In the embodiment of FIG. 3, a positioning fixture of the invention comprises an arcuate inner or lingual flange member 20 (corresponding to flange 12 in FIG. 1) and two separate arcuate outer or buccal flange members 21-22. The two buccal members 21-22 separably meet at the front center of the course of the jaw, and their molar (distal) ends are flexibly connected to the corresponding ends of lingual member 20, via generally U-shaped wires 23—23' having end-embedment in members 20-21 and 20-22 respectively; the wire connections 23—23' will be understood to provide additional means of tooth anchorage or of orthodontic force application to a tooth, for example, to a molar. Each of the buccal members 21 (22) has a small integrally formed half-stud projection 24 (25), adapted for selectively removable retention to each other as by a small orthodontic elastic (not shown) applied around both projections 24-25.

As in the first-described embodiment, separate sources 26 (27) of magnetic flux may be embedded in or otherwise carried by members 20-21 (or 20-22) at mutually opposed locations, and the opposed adjacent surfaces of members 20-21 and 20-22 will be understood to be preferably custom-molded to the patient's individual dental buccal/lingual profiles. The technique of such molding may accord with either of the techniques described in connection with FIGS. 2 and 2A, except of course, there is nothing in FIG. 3 to correspond to the occlusal flange 13. This latter fact means more comfortable wearing of the FIG. 3 fixture, for the patient who can use his own teeth; and removal or mere stretching of the elastic retaining band at 24-25 enables simple removal of the fixture, as for cleaning purposes.

The sources 26-27 may again be permanent magnets, being shown as thin and rectangular, and the above-expressed belief as to why the arrangement is therapeutically beneficial continues to apply, it being noted that in FIG. 3, the magnets 26-27 are susceptible to more ready displacement than in FIG. 1, thus enabling at least as much varying magnetic-field action discussed above, in addition to the polarized field which is inherent in the coacting relation of the opposed magnets.

Figure 4:
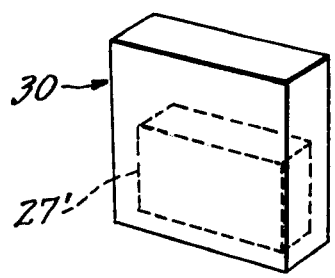
FIG. 4 is an enlarged and simplified view in perspective to show a magnetic component of the fixture of FIG. 3.
Figure 5:
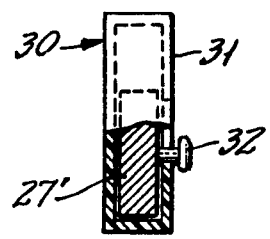
FIG. 5 is an end view of the component of FIG. 4, partly broken-away to show the central vertical section thereof.
Figure 6:
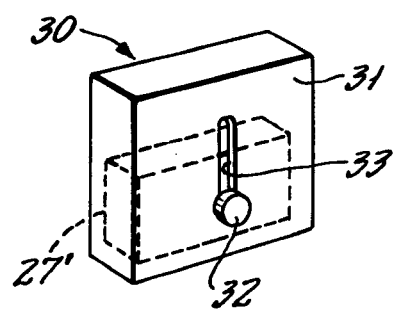
FIG. 6 is another view in perspective to show the other side of the component of FIG. 4.

FIGS. 4, 5 and 6 are directed to a modified magnetic element which may be understood to be in substitution for the lingual-flange magnet 27 of FIG. 3. The point in FIGS. 4, 5 and 6 is that a permanently polarized magnet 27' carried by lingual flange member 20 shall be movable with respect to member 20. To this end, a rectangularly prismatic casing 30, as of bio-compatible acrylic material, is embedded in or otherwise mounted locally to the lingual flange member 20 as to expose its inner face 31 at the lingual side of flange member 20. The inner surfaces of casing 30 establish a guide for ready vertical displaceability of magnet 27', and means such as a headed stud 32 fixed to magnet 27' extends through a vertically short slot 33 in the lingual wall 31, poised for ready actuation by the tongue of the patient. Thus, with the embodiment of FIG. 3, modified to include the movable magnet 27' of FIGS. 4 to 6, greater and more frequent movement of magnets 26-27' is possible, with attendant enhancement of the voltage and current levels induced in affected tissues and/or cells.

Figure 7:
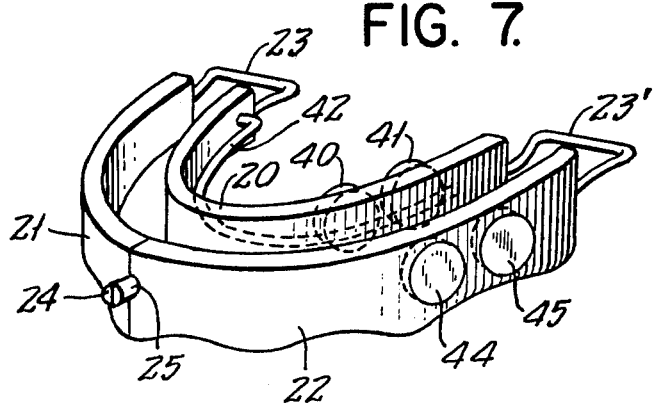
FIG. 7 is a view similar to FIGS. 1 and 3, to show a further embodiment.
Figure 8:
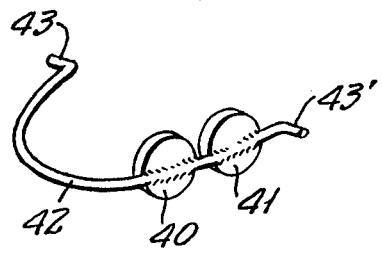
FIG. 8 is a perspective view to show a magnetic component of the fixture of FIG. 7.

Much of what is shown in the embodiment of FIG. 7 corresponds to what has been described for FIGS. 3 to 6, and therefore the same reference numerals are used for corresponding parts. The point of difference in FIG. 7 is that a different means is employed to permit tongue-actuated displacement of one or more sources of magnetic flux. In the form shown, a pair of laterally adjacent permanent-magnet discs 40-41 is carried by an arcuate bail 42 of archwire, as of stainless steel, having outwardly bent ends 43—43' (FIG. 8) which are pivotally referenced to local bearings (holes) at the molar ends of lingual flange member 20. Two similar magnet discs 44-45 are fixedly positioned in similar adjacency on one (22) of the buccal flange members, in coacting opposition to the movable magnet discs 40-41. Corresponding pole faces of magnets 40-41 should face in the same direction, and corresponding pole faces of magnets 44-45 should face in the same direction. And whether the polarities of magnets 40-41 should be in flux-aiding or flux-opposing relation to tne polarities of magnets 44-45 is subject to considerations discussed above for polarity relationships in the embodiment of FIGS. 1 and 2. The use of multiples of magnets in laterally adjacent array, as in the case of magnets 40-41 and 44-45 in FIG. 7, will be understood merely to extend the antero-posterior span of the described range of therapeutic action.

Figure 9:
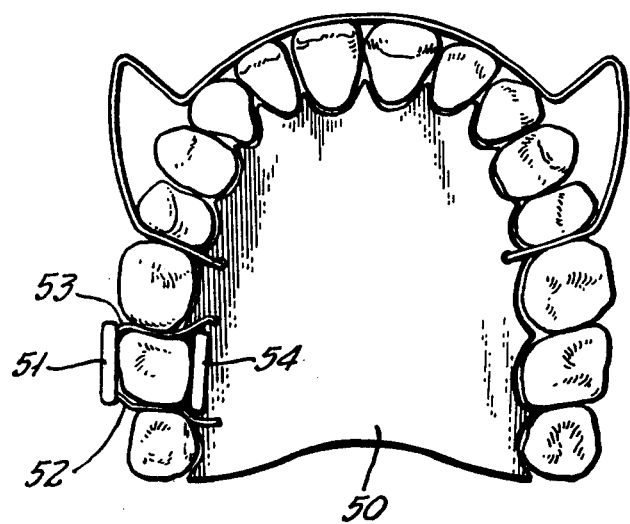
FIG. 9 is a simplified plan view of a dental plate incorporating magnetic means of the invention.

FIG. 9 illustrates application of the invention to a dental plate 50, which may be of the well-known Hawley variety, wherein a buccal magnet 51, protectively embedded as in an acrylic mount or casing is attached to plate 50 via wires 52-53 which span the tooth region to be treated. A coacting lingual magnet 54 is similarly encased and may be mounted for hinge action to posterior regions of plate 50, as described for the arcuate wire 42 and its magnet(s) in FIGS. 7 and 8; however, in the form shown, magnet 54 will be understood to have been received in a suitable local opening cut into and through plate 50, being suitably bonded in place.

The described embodiments of the invention will be seen to achieve the stated objects. These embodiments will be understood to be specifically applicable to various different patient requirements. For example, the embodiment of FIGS. 1 and 2 is more suitable (than those of FIGS. 3 and 7) for children as distinguished from older patients, for the reason that in children the lateral walls of teeth are less relieved or undercut, thus making for easy snap-action application and removal of the fixture. On the other hand, for the more undercut nature of teeth in older persons, the three-member articulated supports of FIGS. 3 and 7 are not only more comfortable but also more easily manipulated, for application or for removal.

In all three of the embodiments of FIGS. 1, 3 and 7, it will be understood that the custom-fit of the positioning fixture includes appropriate undulated contouring of the base profile, as by scissors-cut of the skirt 19 of buccal flange 11 in FIG. 1, to provide maximum overlap with the alveolar ridge, without chafing contact with the gums.

The embodiments of FIGS. 1, 3 and 7 will be seen to serve primarily for periodontal therapy and alveolar-ridge maintenance in edentulous patients, all such treatments being non-invasive. These embodiments also have application for bone augmentation, in the case of boneimplant surgery in the alveolar ridge. And the various embodiments are illustrative of use of the invention in an oral cavity which is also undergoing orthodontic therapy.

Various permanent-magnet materials are discussed in said copending parent application Ser. No. 322,423 and therefore their discussion need not be repeated. We merely state our present preference for SmCo as the magnet material and indicate our preference that each such magnet element be protectively coated with biocompatible material, such as an acrylic.

While the invention has been described in detail for preferred embodiments, it will be understood that modification may be made without departing from the scope of the invention. For example, the particular lingual-magnet suspensions of FIGS. 3 to 6 and 7 will be understood to be further optionally applicable to FIG. 1, in place of the fixed lingual magnet 16.

Further, by way of example, although usage of plural magnets has been described in the context of all such magnets being permanently polarized, it is not necessary that they all be polarized to achieve a beneficial orthodontic or osteogenic or periodontic result. For orthodontic purposes, it is sufficient that one permanent magnet or other source of magnetic flux be established and that one or more elements of magnetic-flux conducting material serve for attractive coaction therewith. And for an osteogenic or periodontic result, it is again sufficient to employ a single source of magnetic flux, for magnetic-field variation as a function of relative movement between one of the elements as the source and the other (or another) of the elements as a means of parasitic coaction with the source element. Thus, reference herein to plural polarized magnet elements reacting with each other merely states a preferred relationship, and non-polarized parasitic reaction of the character indicated is included within the compass of the invention.

It is also to be understood that the expression "non-invasive" as used herein applies to the fact that magnetic fields and changing magnetic fields, as the same are exposed to tooth, bone and other body tissue, are surgically non-invasively applied. The expression "non-invasive" as used herein thus does not preclude applicability of magnetic fields of the invention to tooth, bone or other body tissue which may have been surgically implanted, as for reasons of bone grafting or other reinforcement.

What is claimed is:

1. As an article of manufacture, a unitary intra-oral positioning fixture for use in orthodontic and/or periodontal therapy and bone augmentation, said fixture comprising upstanding buccal and lingual flange members of magnetically transparent material adapted respectively for confronting conformance with the buccal and lingual sides of teeth and in overlap with an associated alveolar-bone region requiring osteogenesis and soft-tissue repair, means compliantly interconnecting said flange members in a manner to permit their selectively removable fixation to span said region, and means including separate polarized sources of magnetic flux carried by said buccal and lingual flange members in mutually facing relation and magnetically coacting with each other via said region.

2. The article of claim 1, in which said flange members establish therebetween a channel which is continuous for substantially the full extent of the maxillary or mandibular arch of a human being.

3. The article of claim 1, in which said lingual flange member extends continuously for substantially the full extent of the maxillary or manidublar arch of a human being, and in which said buccal flange comprises separably connectable arcuate portions having separate compliant connection to said lingual flange.

4. The article of claim 3, in which said buccal flange member extends continuously for substantially said full extent when said portions are interconnected.

5. The article of claim 1, in which opposed adjacent surfaces of said flange members are in contoured conformance with confronting adjacent buccal and lingual profiles of said region.

6. The article of claim 1, in which said material is a compliantly yieldable bio-compatible material.

7. The article of claim 1, in which said material is bio-compatible and is selected from the group which includes acrylic, epoxy, urethane and latex materials.

8. The article of claim 1, in which each of said sources is a permanent magnet oriented to establish a magnetically polarized region through said region.

9. The article of claim 8, in which said magnets are oriented in mutually flux-aiding relation.

10. The article of claim 8, in which said magnets are oriented in mutually flux-opposing relation.

11. The article of claim 1, in which the lingually mounted one of said magnets is mounted for displacement in a direction generally transverse to the direction of coaction through said region.

12. The article of claim 11, in which the lingually mounted magnet is movable in a vertical guide having fixed relation to the lingual flange member, and tongue-engageable means on said lingually mounted magnet for movably actuating the same in its vertical guide.

13. The article of claim 11, in which the lingually mounted magnet is fixed to an arch bar which courses the lingual side of the lingual flange and which is pivotally connected at its ends to the respective distal ends of the lingual flange member.

14. The article of claim 1, in which the means compliantly interconnecting said flange members is a labial flange integrally formed with said buccal and lingual flanges.

15. The article of claim 8, in which each of said magnets is relatively thin in the direction of its polarization axis.

16. The article of claim 15, in which each of said magnets is a generally circular disc.

17. The article of claim 15, in which each of said magnets is generally rectangularly prismatic.

18. As an article of manufacture, a unitary intraoral positioning fixture for use in orthodontic and/or periodontal therapy and bone augmentation, said fixture comprising a lingual base of magnetically transparent material with a polarized source of magnetic flux mounted thereto in adjacency to the lingual side of a region of alveolar bone requiring osteogenesis, bone-remodeling and soft-tissue repair, and a second source of magnetic flux carried by said base and mounted for adjacency to the buccal side of said region and oriented for magnetic coaction with said first source via said region.

19. The article of claim 18, in which said base is the lingual flange of a fixture which integrally further includes labial and buccal flanges to define a channel adapted to span opposed areas of alveolar bone, said second source being mounted to said buccal flange.

20. The article of claim 18, in which said base is a dental plate and said second source is mounted thereto via interdental wire.

21. The article of claim 20, in which said dental plate is an orthodontic appliance.

22. As an article of manufacture, a unitary intraoval positioning fixture for use in orthodontic and/or periodontal therapy and bone augmentation, said fixture comprising upstanding buccal and lingual and flange members of magnetically transparent material adapted respectively for confronting conformance with the buccal and lingual sides of teeth and in overlap with an associated alveolar-bone region requiring osteogenesis, bone-remodeling in general and soft-tissue repair, means compliantly interconnecting said flange members in a manner to permit their selectively removable fixation to span said region, and means including separate elements of magnetic-flux-conducting material carried by said buccal and lingual flange members, one of said elements being permanently polarized and magnetically coacting with the other of said elements via said region.

23. The article of claim 22, in which the other of said elements is also permanently polarized.

* * * * *